US006000492A

United States Patent [19]

Puthuff et al.

[11] Patent Number: 6,000,492

[45] Date of Patent: Dec. 14, 1999

[54] CERUMEN BLOCK FOR SOUND DELIVERY SYSTEM

[75] Inventors: Steven H. Puthuff, Saratoga; David L. Luger, Foster City; Jon C. Taenzer, Los Altos, all of Calif.

[73] Assignee: Resound Corporation, Redwood City, Calif.

[21] Appl. No.: 09/106,080

[22] Filed: Jun. 29, 1998

[51] Int. Cl.[6] ........ A61B 7/02

[52] U.S. Cl. ........ 181/135; 381/325

[58] Field of Search ........ 181/128, 129, 181/130, 135; 381/322, 325, 328

[56] References Cited

U.S. PATENT DOCUMENTS

| | | | |
|---|---|---|---|
| 3,536,861 | 10/1970 | Dulavy . | |
| 3,975,599 | 8/1976 | Johanson . | |
| 3,983,336 | 9/1976 | Malek et al. . | |
| 4,090,040 | 5/1978 | Berland . | |
| 4,450,930 | 5/1984 | Killion . | |
| 4,751,738 | 6/1988 | Widrow et al. . | |
| 4,869,339 | 9/1989 | Barton . | |
| 4,904,078 | 2/1990 | Gorike . | |
| 4,972,488 | 11/1990 | Weiss et al. | 381/328 |
| 5,031,219 | 7/1991 | Ward et al. . | |
| 5,033,090 | 7/1991 | Weinrich et al. . | |
| 5,105,904 | 4/1992 | Olsen | 181/128 |
| 5,113,967 | 5/1992 | Killion et al. . | |
| 5,201,006 | 4/1993 | Weinrich . | |
| 5,201,007 | 4/1993 | Ward et al. . | |
| 5,276,739 | 1/1994 | Krokstad et al. . | |
| 5,278,912 | 1/1994 | Waldhauer . | |
| 5,401,920 | 3/1995 | Oliveira | 181/135 |
| 5,488,205 | 1/1996 | Major . | |
| 5,488,668 | 1/1996 | Waldhauer . | |
| 5,500,902 | 3/1996 | Stockhan, Jr. et al. . | |
| 5,524,056 | 6/1996 | Killion et al. . | |

OTHER PUBLICATIONS

Richard Navarro, et al. "An Ultrasonic Method of Cleaning Cerumen–Occluded Receivers," The Hearing Journal, Jun. 1998, vol. 51, No. 6, p. 62.

Product Marketing Information, "The Ad–hear™ Wax Guard is the Easiest Way to Keep Your Hearing Aid Clean," Hearing Components, Inc., date unknown.

Product Marketing Information, "Rid Wax," Oto–Med Technologies, Inc., Oct. 1997.

Product Marketing Information, "Wax Buster," Knowles Electronics, Inc., date unknown.

Product Marketing Information, "Wax Shield," Knowles Electronics, Inc., date unknown.

*Primary Examiner*—Khanh Dang
*Attorney, Agent, or Firm*—Burns, Doane, Swecker & Mathis, L. L. P.

[57] ABSTRACT

An earpiece for a sound delivery system has a sound output port for delivering sound into the ear canal of the user. A cerumen block is provided to prevent cerumen or earwax from blocking the sound output port of the earpiece. The cerumen block is formed by a small flap of material which covers the sound output port and blocks cerumen from entering the sound output port in a closed position while allowing sound to pass around the flap and enter the ear canal in an open position. A resilient hinge returns the cerumen flap to the open position once the earpiece has been placed within the ear canal.

20 Claims, 6 Drawing Sheets

FIG._1
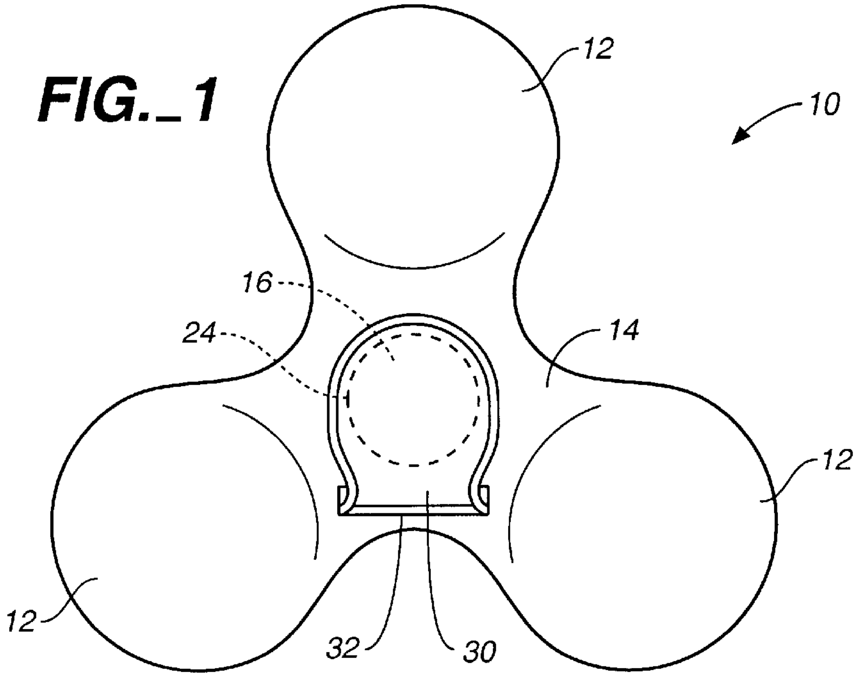
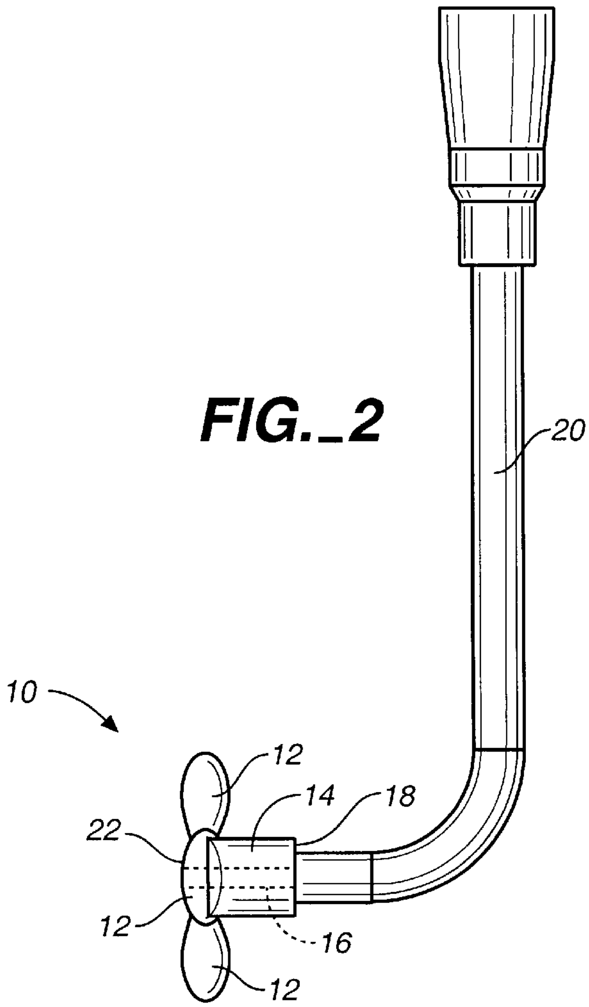
FIG._2

CERUMEN BLOCK FOR SOUND DELIVERY SYSTEM

BACKGROUND OF THE INVENTION

1. Field of the Invention

The present invention relates to a cerumen block for a sound delivery system such as a hearing aid, a communications device, or a multimedia device, and more particularly, the invention relates to an earpiece having a cerumen block for improved delivery of sound into the ear canal.

2. Brief Description of the Related Art

Sound delivery systems such as hearing aids, cellular telephones, and other sound transmitting systems employing earpieces are utilized to deliver sounds directly to the ear canal of the user. Such sound delivery systems include those worn by police, firefighters, secret service agents, and the like to receive sound transmissions from a remote location. Other sound delivery systems include the class of hearing aids which are used by the hearing impaired to amplify and process sounds. Traditional hearing aids include "in the ear" (ITE) hearing aid devices inserted into the ear of the user, "in the canal" (ITC), "completely in the canal" (CIC), and "behind the ear" (BTE) hearing aid devices which are attached behind the ear of the user. The BTE hearing aid devices generally include a flexible plastic tube connecting an amplification and processing device mounted behind the ear to an eartip positioned within the ear canal.

Many different types of eartips are available for fixing an end of a sound transmitting tube in the ear canal. Eartips may be custom made to fit within the ear canal of a particular user, however, these custom made eartips are expensive and can block the ear canal almost entirely causing a problem known as the occlusion effect. Other types of eartips include stock members which are generally used during a trial period when a hearing aid is being tested or while an ear mold is being made. These stock eartips may be formed of hard materials, rubbery materials, or foam. However, any eartip which is placed within the ear canal will have problems of blockage of the eartip sound output ports by cerumen (earwax).

Cerumen blockage of the sound output ports of an earpiece causes sound degradation and eventual failure of the sound delivery system to deliver sound to the ear canal. This degradation and eventual failure due to cerumen blockage is the most common cause of failure in sound delivery systems such as hearing aids. There are many different approaches commercially available for preventing the cerumen blockage of hearing aid sound output ports. One such blockage preventing method includes a sound transparent membrane which allows sound to pass through while blocking cerumen. Because of the thinness required of the sound transparent membrane to prevent sound attenuation, the membrane tends to be delicate and to tear or puncture easily.

Another type of cerumen blockage prevention system includes a mechanical assembly which can be periodically actuated to eject collected cerumen from the sound output ports to clear the output ports. One such mechanical actuated assembly includes a spring loaded cylindrical output port which slides over a pin to eject cerumen. The mechanical actuated assemblies for ejection of cerumen are complex and require periodic actuation to remove cerumen buildup. Another type of blockage protector is a replaceable "band aid" type protector which requires periodic replacement. The "band aid" cerumen protector includes a porous piece of material such as foam having pressure sensitive adhesive which is used to secure the foam over a sound output port. These "band aids" fill up with cerumen, blocking the sound but are easily peeled off and replaced. Thus, these devices must be maintained and there is an associated expense of periodic replacement. Finally, acoustic labyrinths have been used in the sound output ports of earpieces to reduce cerumen blockage. These acoustic labyrinths slow the occurrence of cerumen blockage but will still become clogged over time.

Accordingly, it would be desirable to address the problem of cerumen blockage of sound delivery output ports by a simple, reliable, and effective cerumen blockage device.

SUMMARY OF THE INVENTION

The present invention relates to a sound delivery system having an earpiece with a sound output port for delivery of sound into the ear canal of the user. A cerumen block is formed by a small flap of material which blocks cerumen from entering the sound output port and allows sound to pass around the flap to enter the ear canal.

In accordance with one aspect of the present invention, an earpiece for delivery of sounds to an ear canal includes a body configured to be received within the ear canal, a sound output port in the body for delivery of sounds to the ear canal, and a flap of resilient material secured to the body by at least one hinge and extending over the output port. The flap has a closed position in which the flap prevents cerumen from entering the sound output port and an open position at which a sound transmitting space is provided between the flap and the output port.

In accordance with another aspect of the present invention, an earpiece for use in a sound delivery system includes a body configured to be received within an ear canal, the body having a first end for attachment to a sound delivery tube and a second end having a sound output port and a resilient cerumen blocking flap extending from the body over the sound output port. The flap has an occluding position in which the flap prevents cerumen from entering the output port and a relaxed position in which sound passes out of the output port and around the flap.

The present invention provides the advantages of preventing cerumen blockage of the sound output port of an earpiece with a simple, reliable, and effective cerumen block.

BRIEF DESCRIPTION OF THE DRAWING FIGURES

The invention will be described in greater detail with reference to the preferred embodiments illustrated in the accompanying drawings, in which like elements bear like reference numerals, and wherein:

FIG. 1 is a front view of an eartip having a cerumen block according to the present invention;

FIG. 2 is a side view of the eartip of FIG. 1 mounted on a sound delivery tube;

DETAILED DESCRIPTION OF THE PREFERRED EMBODIMENTS

Figure 3:
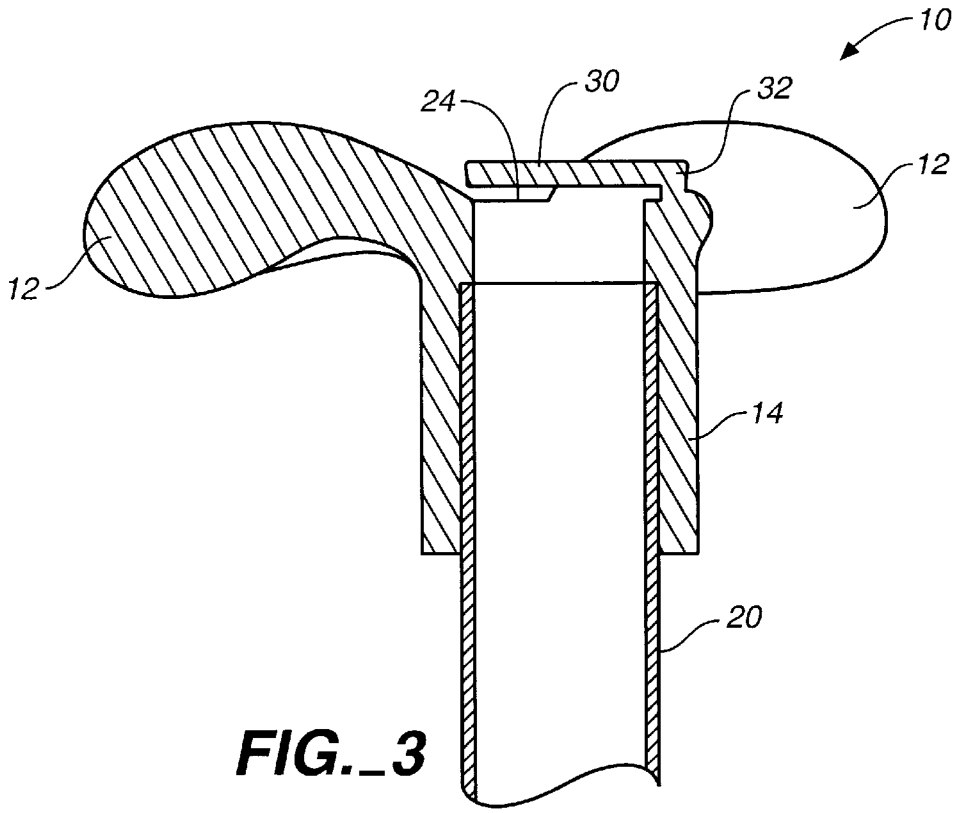
FIG. 3 is a side cross sectional view of the eartip with a cerumen block according to a first embodiment of the invention.

The term "earpiece" as used herein includes any sound delivery device which is placed at least partially within the ear canal such as an ITE hearing aid, an eartip of a BTE hearing aid device, as well as the in the ear components of other communications systems. The cerumen blockage device according to the present invention is applicable to any earpiece.

The earpiece illustrated in FIGS. 1 and 2 is a flower shaped eartip 10 having three petals 12 extending from a central portion or base 14. As shown in FIG. 2, the eartip 10 may be connected to a sound delivery tube 20 which extends from a behind the ear device into the ear canal. The sound delivery tube 20 is connected to a receiver, amplifier, or other sound processing device which may be positioned behind the user's ear. The eartip 10 may be mounted on the sound delivery tube 20 by any known method such as over-molding, adhesive, a snap-fit connection, and the like. Alternatively, the eartip 10 and sound delivery tube 20 may be molded together in one piece. The eartip 10 has a sound delivery channel 16 extending from a first end 18 of the eartip which is connected to the sound delivery tube 20 to a second end 22 of the eartip where the channel forms a sound delivery output port 24. The sound delivery output port 24 is covered by the cerumen block or flap 30.

The cerumen flap 30 is formed of a resilient material and is connected to the eartip 10 by a hinge 32. The cerumen block 30 is preferably a small flap of soft, rubbery, resilient material which is hinged to the eartip 10 at one or more sides and is movable from an open position to a closed position. As the eartip 10 is inserted into the ear cannel, any cerumen within the ear cannel which would otherwise enter and block the sound output port 24 of the eartip is pushed aside by the cerumen flap 30 which is simultaneously pushed to a closed position by contact with the cerumen or the ear canal itself. The output port 24 of the eartip 10 is temporarily sealed by the cerumen flap 30 which is pushed to a closed position during insertion of the eartip. After insertion, the cerumen flap 30 relaxes back to the original position illustrated in FIG. 3, unsealing the output port 24 and allowing sound to enter the ear canal through the gap between the cerumen flap and the base 14 of the eartip.

FIG. 3 is a side cross sectional view of the eartip having the cerumen flap 30 in a relaxed unsealing or opened position over the output port 24 of the eartip. In this relaxed position, the sound is permitted to pass between the edges of the output port 24 and the cerumen flap 30. The cerumen flap 30 is somewhat larger in diameter than the output port 24 so that the flap is capable of completely sealing the output port and will not be forced into the output port.

Figure 4:
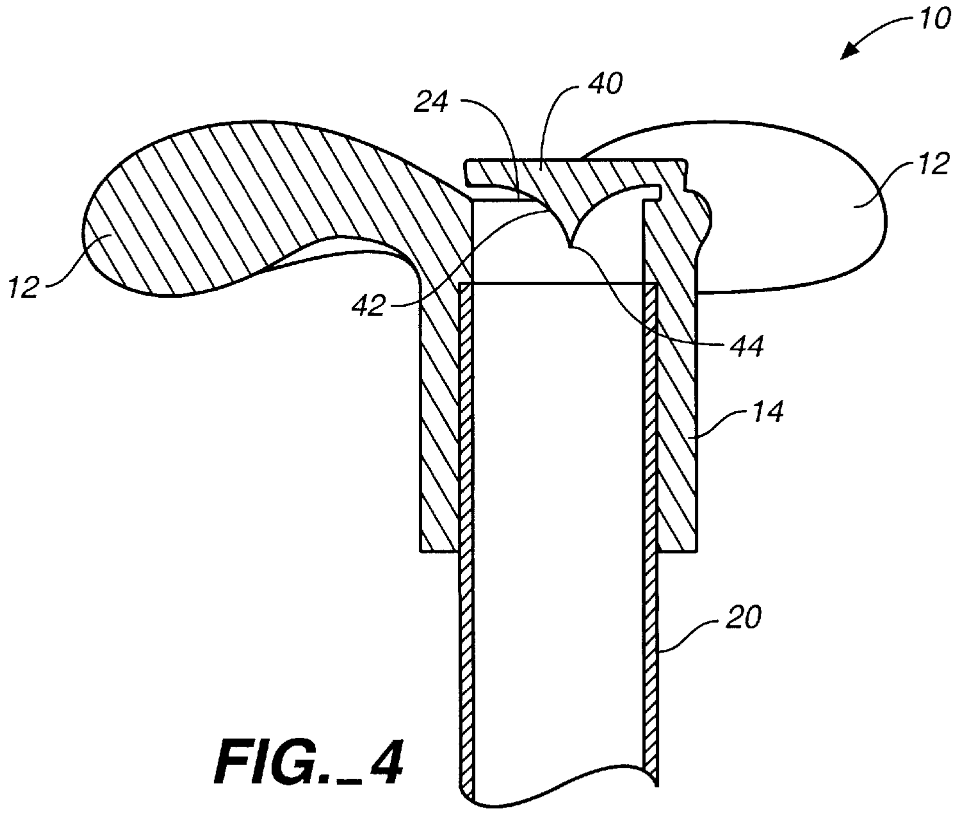
FIG. 4 is a side cross sectional view of the eartip with a cerumen block according to a second embodiment of invention.
Figure 5:
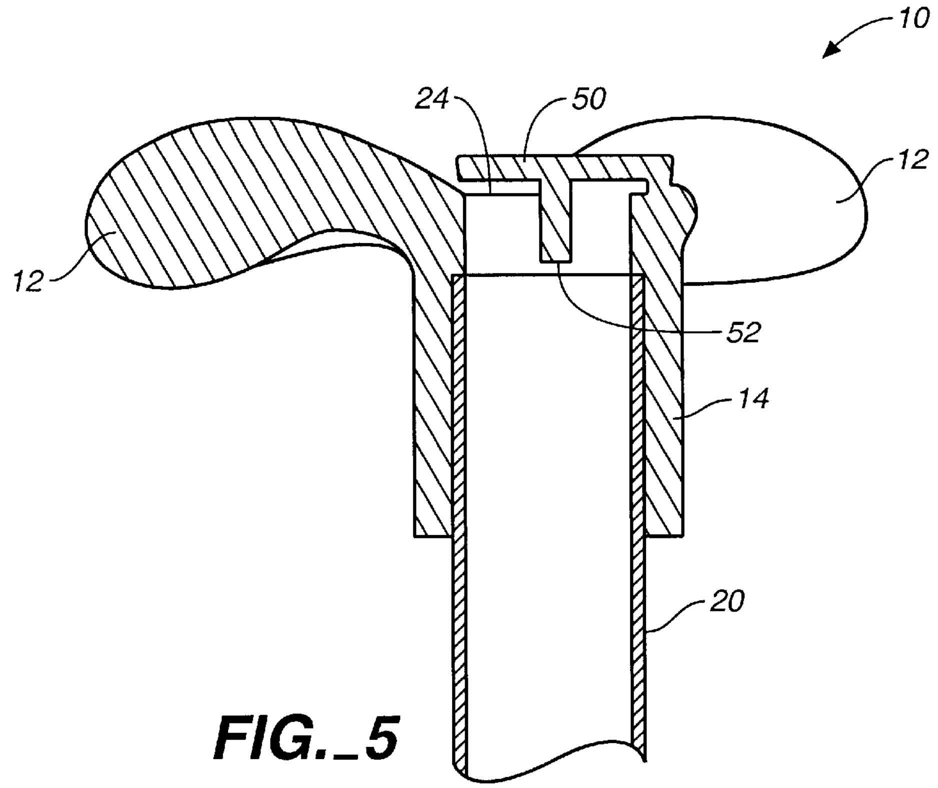
FIG. 5 is a side cross sectional view of the eartip with a cerumen block according to a third embodiment of the invention.
Figure 6:
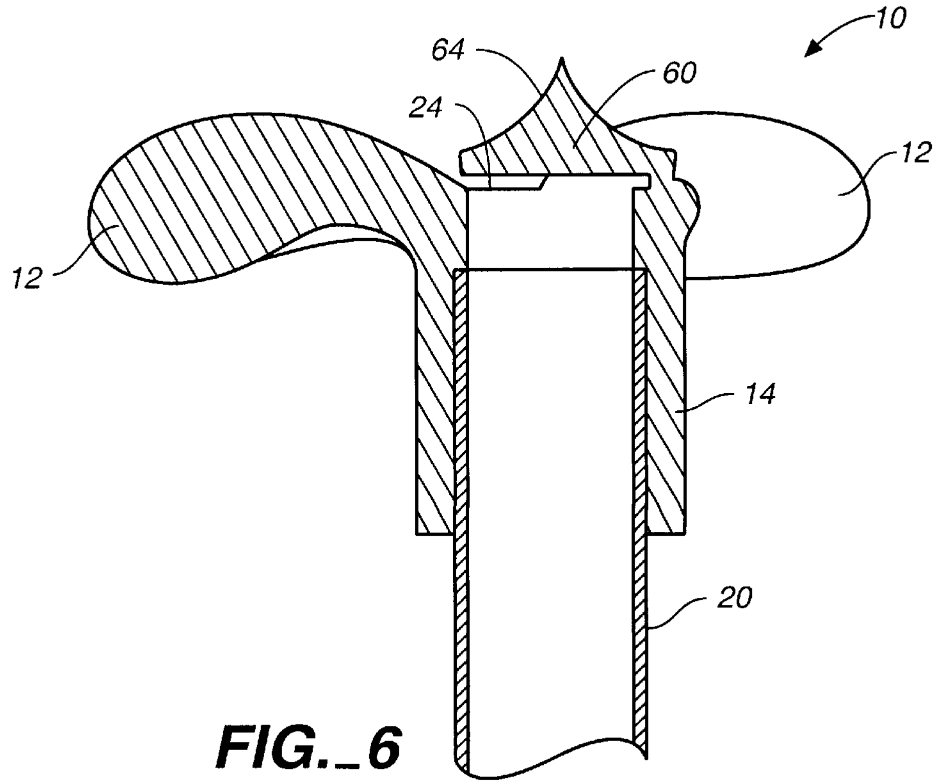
FIG. 6 is a side cross sectional view of the eartip with a cerumen block according to a fourth embodiment of the invention.

Several alternative embodiments of a cerumen flap with additional advantageous features are illustrated in FIGS. 4–6. For example, FIG. 4 illustrates an eartip having a cerumen flap 40 with a continuous concave inner surface 42 coming to a point 44 within the output port 24. The concave inner surface 42 of the flap operates to better direct and couple sound out of the output port 24 between the cerumen flap 40 and the base 14 of the eartip.

FIG. 5 illustrates a further alternative embodiment of an eartip 10 having a cerumen flap 50 according to the present invention. The cerumen flap 50 includes a guide member 52 which extends from the cerumen flap into the output port 24 to maintain the cerumen flap in a centered arrangement on the output port during use. The guide member 52 is illustrated as a pin, however, the guide member may have alternative configurations including a plurality of ribs, a star shape, a conical shape, or the like for maintaining the cerumen flap in a generally centered orientation over the output port 24.

FIG. 6 illustrates a further embodiment of an eartip having a cerumen flap 60 with a cerumen deflector 62. The cerumen deflector 62 has concaved or angled surfaces 64 which deflect the cerumen to the sides and away from the output port 24 of the eartip 10 as the eartip is inserted into the ear canal.

Figure 7:
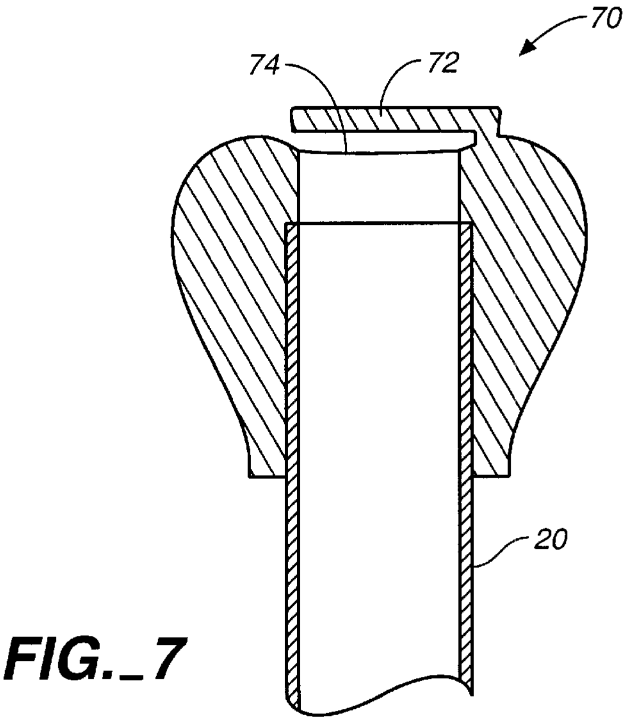
FIG. 7 is a side view of a bud shaped eartip with a cerumen block according to the present invention.

FIG. 7 illustrates an alternative embodiment of an eartip 70 of a bud shape having a cerumen flap 72 extending over a sound output port 74 of the eartip. The flower shaped eartips of FIGS. 1–6 and the bud shaped eartip of FIG. 7 are examples of some of the earpiece shapes which may be used with the present invention. Many other earpiece shapes may also be used including the guppie shaped eartip illustrated in U.S. Provisional Patent Application Ser. No. 60/053,031 filed on Jul. 18, 1997, which is incorporated herein by reference in its entirety. Other shapes and constructions of custom earpieces, hearing aid housings, and stock earpieces may also incorporate the cerumen block according to the present invention.

Figure 8:
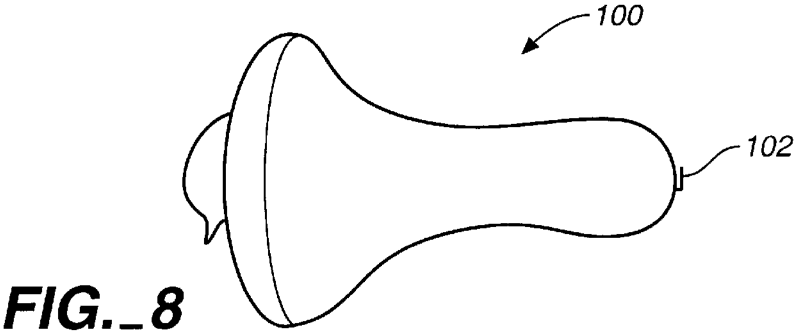
FIG. 8 is a side view of an "in the ear" (ITE) hearing aid with a cerumen block.
Figure 9:
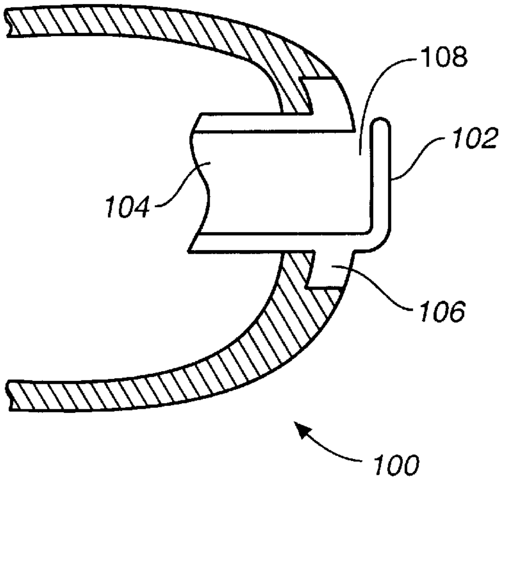
FIG. 9 is a side cross sectional view of the output port of the ITE hearing aid of FIG. 8.

FIGS. 8 and 9 illustrate an ITE hearing aid 100 with a cerumen flap 102 according to the present invention. As shown in the enlarged cross sectional view of FIG. 9, an output port 108 of the earpiece 100 is formed by a molded exit tube 104 of an elastomeric material. The exit tube 104 is mounted by an annular flange 106 on a housing of the ITE hearing aid 100. The cerumen flap 102 is molded with the exit tube 104 and extends over the sound output port 108 of the earpiece.

Figure 10:
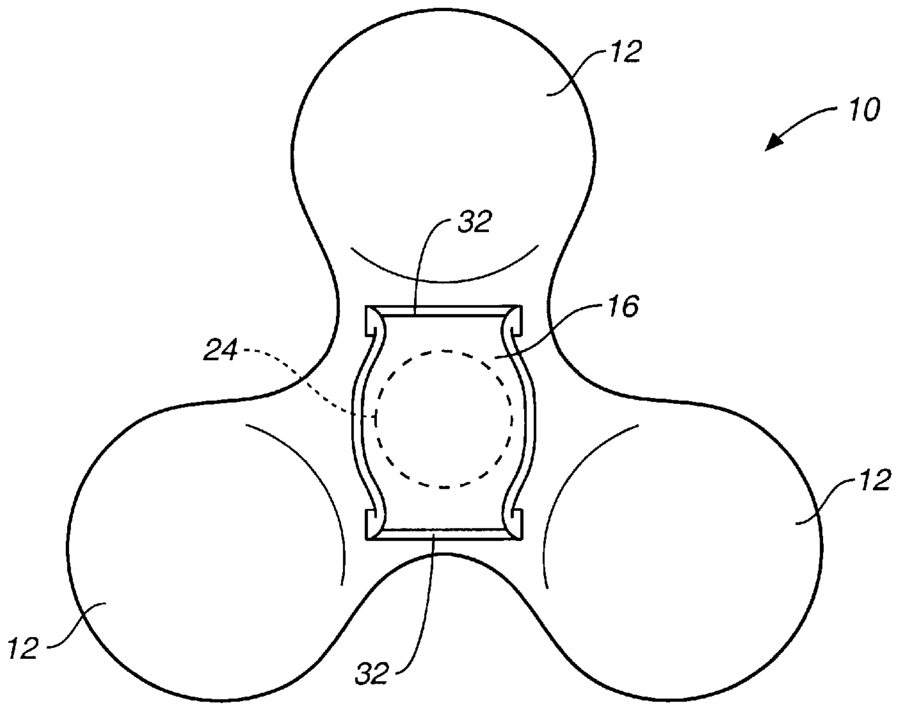
FIG. 10 is a front view of the eartip having a cerumen block attached to the eartip body at two hinge locations.
Figure 11:
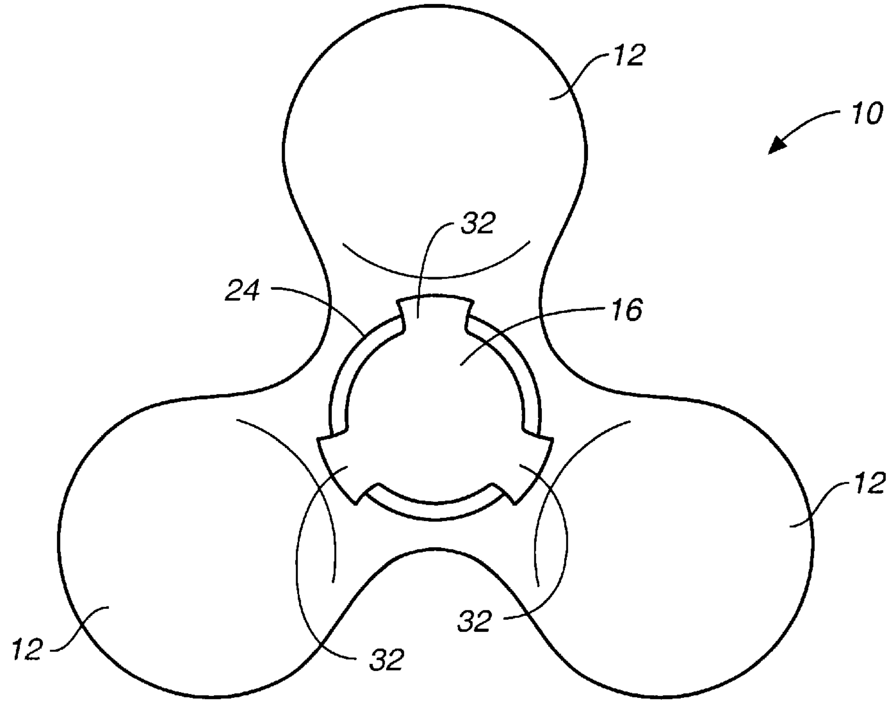
FIG. 11 is a front view of the eartip having a cerumen block attached to the eartip body at three hinge locations.

FIGS. 10 and 11 illustrate further embodiments of the present invention incorporating cerumen flaps 16 with a plurality of hinges 32. In these embodiments with a plurality of hinges 32, the cerumen flap 16 moves from an open or relaxed position to a closed positioned in which the flap prevents cerumen from entering the sound output port 24 by sealing the output port. The cerumen flap 16 is permitted to move from the open to the closed position by flexing of the flexible hinges 32.

As illustrated in the embodiments of FIGS. 1–8, the cerumen flap is preferably larger that the sound output port of the earpiece, such that the sound output port is entirely blocked by the cerumen flap in the closed position. As illustrated in FIG. 11, the cerumen flap 16 may have a diameter which is equal to or somewhat smaller than the diameter of the output port 24. In this case, the cerumen flap 16 is prevented from becoming pushed into the sound output port 24 by the hinges 32. The smaller cerumen flap 16 allows additional space to be provided between the flap and the eartip body 14 for the sound to pass out of the eartip while substantially preventing cerumen from entering the sound output port.

Figure 12:
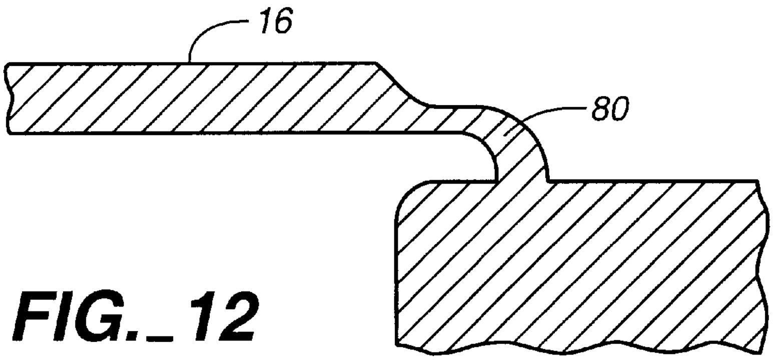
FIG. 12 is a side cross sectional view of a first embodiment of a hinge.
Figure 13:
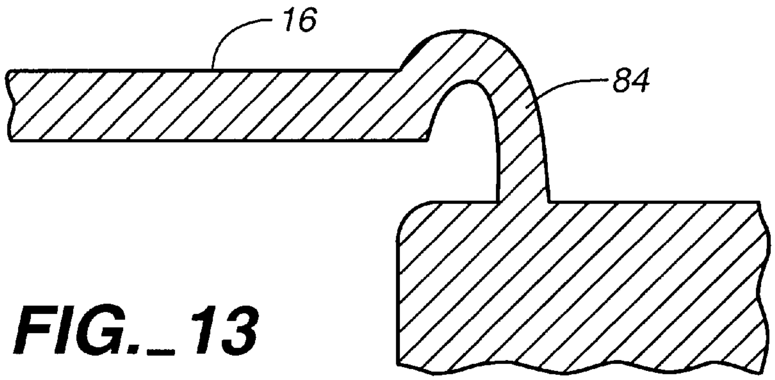
FIG. 13 is a side cross sectional view of a second embodiment of a hinge.
Figure 14:
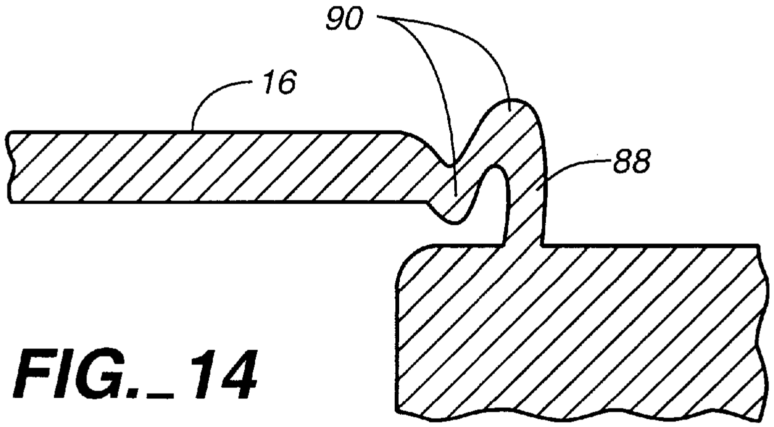
FIG. 14 is a side cross sectional view of a third embodiment of a hinge.

FIGS. 12–14 illustrate alternative embodiments of hinge sections for attaching the cerumen flap 10 according to the present invention to an earpiece such that the flap is allowed to move from an open position or relaxed position to a closed positioned in which the flap prevents cerumen from entering the sound output port of the earpiece. FIG. 12 illustrates a hinge 80 which is formed as the thin flexible section of resilient material. This hinge 80 can have many shapes and may be either the same thickness or somewhat thinner than the cerumen flap 16 itself. The hinge 80 may be formed of the same material as either the cerumen flap 10 or the earpiece body or may be formed of a different material. The flexibility of the hinge 80 may be varied by changing the material, the shape, and/or the thickness of the hinge.

FIG. 13 illustrates an alternative embodiment of a rolled hinge 84. The rolled hinge 84 allows the cerumen flap to move in a substantially linear path. Particularly, the rolled hinge 84 when used in the embodiments of FIG. 10 or FIG. 11 will change curvature to move between the open and closed positions. FIG. 14 illustrates a further alternative embodiment including a corrugated hinge section 88 having a plurality of bends 90. The corrugated hinge 88 will allow the cerumen flap to move between the open and closed positions in a substantially linear path.

The earpiece according to the present invention may be formed by molding the earpiece including the cerumen flap and hinge as a single piece. Alternatively, the cerumen flap and hinge can be molded separately from the earpiece and attached to an earpiece which is of a different material from the cerumen flap. For example, if a custom ear mold is used a molded cerumen flap may be formed separately and attached by a hinge to cover the output port of the custom ear mold. The material of the cerumen flap and hinge is preferably a resilient material such as soft plastic, silicone rubber, Teflon, or the like. The chosen material once cured, is preferably chemically inert and relatively uneffected by changes in temperature, by exposure to light, and by exposure to cerumen. The use of Teflon provides the added advantage of preventing cerumen from sticking to the earpiece, however, the low friction surface of the Teflon earpiece may allow the earpiece to slip out of the ear canal.

While the invention has been described in detail with reference to the preferred embodiments thereof, it will be apparent to one skilled in the art that various changes and modifications can be made and equivalents employed, without departing from the present invention.

What is claimed is:

1. An earpiece for delivery of sounds to an ear canal comprising:

a body configured to be received within the ear canal;

a sound output port in the body for delivery of sounds to the ear canal;

at least one hinge; and a flap of resilient material secured to the body by the at least one hinge and extending over the output port, the flap having a closed position in which the flap prevents cerumen from entering the sound output port and an open position at which a sound transmitting space is provided between the flap and the output port.

2. The earpiece according to claim 1, wherein the body, the flap, and the hinge are molded as a single piece from a resilient material.

3. The earpiece according to claim 2, wherein the resilient material is silicone rubber.

4. The earpiece according to claim 1, wherein the flap is secured to the body by at least two hinges.

5. The earpiece according to claim 1, wherein the flap in the closed position covers the entire output port.

6. The earpiece according to claim 1, wherein the flap includes a concave sound deflecting surface on a side adjacent the sound output port.

7. The earpiece according to claim 1, wherein the flap includes a guide for guiding the flap to cover the output port in the closed position.

8. The earpiece according to claim 1, wherein the flap includes a wax deflecting surface on a side of the flap away from the output port.

9. The earpiece according to claim 1, wherein the at least one hinge has a plurality of preformed bends.

10. The earpiece according to claim 1, wherein the sound output port is formed by an exit tube which is molded in one piece with the flap and wherein the body is an "in the ear" hearing aid.

11. The earpiece according to claim 1, wherein the flap moves from the open position to the closed position automatically on contact with cerumen.

12. An earpiece for use in a sound delivery system comprising:

a body configured to be received within an ear canal, the body having a first end for attachment to a sound delivery tube and a second end having a sound output port; and a resilient cerumen blocking flap extending from the body over the sound output port, the flap movable from an occluding position in which the flap prevents cerumen from entering the output port to a relaxed position in which sound passes out of the output port and around the flap.

13. The earpiece according to claim 12, wherein the body, the flap, and the hinge are molded as a single piece from a resilient material.

14. The earpiece according to claim 12, wherein the flap is secured to the body by at least two hinges.

15. The earpiece according to claim 12, wherein the flap in the closed position covers the entire output port.

16. The earpiece according to claim 12, wherein the flap includes a concave sound deflecting surface on a side adjacent the sound output port.

17. The earpiece according to claim 12, wherein the flap includes a guide for guiding the flap to cover the output port in the closed position.

18. The earpiece according to claim 12, wherein the flap includes a wax deflecting surface on a side of the flap away from the output port.

19. The earpiece according to claim 12, wherein the at least one hinge has a plurality of preformed bends.

20. The earpiece according to claim 12, wherein the flap moves from the relaxed position to the occluding position automatically on contact with cerumen.

* * * * *